United States Patent
Henley et al.

(10) Patent No.: US 11,980,336 B2
(45) Date of Patent: May 14, 2024

(54) SYSTEM AND METHOD FOR REMOVING SPECKLE FROM A SCENE LIT BY A COHERENT LIGHT SOURCE

(71) Applicant: DePuy Synthes Products, Inc., Raynham, MA (US)

(72) Inventors: Jeremiah D. Henley, Fair Oaks, CA (US); Joshua D. Talbert, Cottonwood Heights, UT (US); Laurent Blanquart, Westlake Village, CA (US); Donald M. Wichern, Ogden, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/051,378

(22) Filed: Oct. 31, 2022

(65) Prior Publication Data
US 2023/0080490 A1    Mar. 16, 2023

Related U.S. Application Data (60) Continuation of application No. 16/915,765, filed on Jun. 29, 2020, now Pat. No. 11,484,270, which is a
(Continued)

(51) Int. Cl.
| | |
|---|---|
| A61B 1/00 | (2006.01) |
| A61B 1/01 | (2006.01) |
| A61B 1/045 | (2006.01) |
| A61B 1/06 | (2006.01) |
| A61B 1/07 | (2006.01) |
| A61B 5/00 | (2006.01) |
| G02B 23/24 | (2006.01) |
| G02B 27/48 | (2006.01) |

(52) U.S. Cl.
CPC .......... *A61B 1/01* (2013.01); *A61B 1/00009* (2013.01); *A61B 1/00045* (2013.01); *A61B 1/0008* (2013.01); *A61B 1/00096* (2013.01); *A61B 1/00135* (2013.01); *A61B 1/045* (2013.01); *A61B 1/063* (2013.01); *A61B 1/0638* (2013.01); *A61B 1/07* (2013.01); *A61B 5/7203* (2013.01); *A61B 5/7207* (2013.01); *G02B 23/2469* (2013.01); *G02B 27/48* (2013.01)

(58) Field of Classification Search
CPC .......... A61B 1/000095; A61B 1/00045; A61B 1/00096; A61B 1/00135; A61B 1/045; A61B 1/0638; A61B 1/07; A61B 5/7203; A61B 5/7207
See application file for complete search history.

(56) References Cited

U.S. PATENT DOCUMENTS

| | | | | |
|---|---|---|---|---|
| 5,790,724 A | * | 8/1998 | Neuberger | ........... G02B 6/4296 |
| | | | | 250/227.14 |
| 2009/0232438 A1 | * | 9/2009 | Shimotsu | ............... G02B 27/48 |
| | | | | 385/1 |

(Continued)

*Primary Examiner* — Anh T Nguyen
*Assistant Examiner* — Rynae E Boler
(74) *Attorney, Agent, or Firm* — TechLaw Ventures, PLLC; Terrence J. Edwards (57) ABSTRACT

The disclosure extends to methods, devices, and systems for removing speckle from a coherent light source, such as laser light. The methods, devices, and systems help eliminate or reduce speckle introduced from a coherent light source, such as laser light, by utilizing the teachings and principles of the disclosure.

20 Claims, 10 Drawing Sheets

Related U.S. Application Data continuation of application No. 15/063,090, filed on Mar. 7, 2016, now Pat. No. 10,695,003, which is a division of application No. 14/214,388, filed on Mar. 14, 2014, now Pat. No. 10,299,732.

(60) Provisional application No. 61/791,860, filed on Mar. 15, 2013.

(56) References Cited

U.S. PATENT DOCUMENTS

| | | | |
|---|---|---|---|
| 2009/0318758 A1* | 12/2009 | Farr | A61B 90/53 600/112 |
| 2010/0268034 A1* | 10/2010 | Krattiger | A61B 1/00165 600/178 |
| 2013/0003343 A1* | 1/2013 | Sudarshanam | G02B 27/48 362/19 |

* cited by examiner

SYSTEM AND METHOD FOR REMOVING SPECKLE FROM A SCENE LIT BY A COHERENT LIGHT SOURCE

CROSS-REFERENCE TO RELATED APPLICATIONS

This application is a continuation of U.S. patent application Ser. No. 16/915,765, filed Jun. 29, 2020 (now U.S. Pat. No. 11,484,270), which is a continuation of U.S. patent application Ser. No. 15/063,090, filed on Mar. 7, 2016 (now U.S. Pat. No. 10,695,003), and which is a divisional of U.S. patent application Ser. No. 14/214,388, filed on Mar. 14, 2014 (now U.S. Pat. No. 10,299,732), and claims the benefit of U.S. Provisional Application No. 61/791,860, filed Mar. 15, 2013, which are incorporated herein by reference in its entirety, including but not limited to those portions that specifically appear hereinafter, the incorporation by reference being made with the following exception: In the event that any portion of the above-referenced applications are inconsistent with this application, this application supersedes said above-referenced applications.

STATEMENT REGARDING FEDERALLY SPONSORED RESEARCH OR DEVELOPMENT

Not Applicable.

BACKGROUND

With increasing use of laser technology in various applications, the occurrence of speckle effect has increased. The speckle effect refers to a pattern in which there is a random distribution of varying light intensity levels and may occur with coherent light sources. In the case of a coherent light source, such as laser light, a speckle pattern of bright and dark spots appears in the area being lit. It is caused by the interference of many waves of the same frequency, but different phases and amplitudes, combining and resulting is a wave whose amplitude and intensity varies randomly. This occurs when coherent light (light consisting of only one wavelength) is scattered off a rough surface. It should be noted that "rough" refers to the surface texture at a microscopic level. Thus, in minimally invasive surgical (MIS) procedures or applications, all surfaces can be considered rough.

When a coherent light source, such as laser light, is used as the light source for minimally invasive surgical (MIS) or endoscopic procedures, speckle is an undesirable effect as it makes the image appear grainy to a viewer. Conventional light sources for MIS and endoscopy (such as metal halide bulbs, halogen bulbs, xenon bulbs, and light emitting diodes (LEDs)) do not have a speckle pattern because the light has low coherence. Speckle patterns are generally not noticeable from light with low coherence because the amplitude variations tend to average each other out. Despite the speckle pattern, a laser light source may have benefits over conventional light sources, including power efficiency, cost, low heat generation, small size, color pulsing, narrow-band imaging, and the ability to generate controlled light outside the visible spectrum (infrared or ultraviolet). Therefore, a coherent light source system, such as a laser light source system, without the speckle pattern is desirable.

Others have attempted to address the speckle effect with laser light using a variety of methods, each of which essentially lowers the coherence of the light. One of the simplest methods is to place a moving diffuser in the light path. The diffuser can rotate or oscillate and this movement lowers the light coherence. Other methods include systems of mirrors, homogenizing lenses, and/or light guides. A common application of the technology is in laser projectors.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

The disclosure extends to methods, devices, and systems for removing speckle from a coherent light source, such as laser light. The methods, devices, and systems of the disclosure help eliminate or reduce speckle introduced from a coherent light source, such as laser light, by utilizing the teachings and principles of the disclosure. In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "coherent light source" refers to a source of light or electromagnetic radiation that is capable of producing radiation with all of the wavelengths vibrating in-phase. Thus, "coherent light source" includes, but is not limited to, light or radiation consisting of only one wavelength because such light or radiation is considered to be in-phase. Such light sources may include, for example, a laser light source. It will be appreciated that all coherent light sources are intended to fall within the scope of the disclosure.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

Referring now to the figures, it will be appreciated that speckle from a coherent light source, such as laser light, used for endoscopy may be removed by vibrating a fiber optic bundle that carries the light from the light source to a surgical site. The removal of speckle may be achieved by attaching a vibrating mechanism to the fiber optic bundle at some location along the length of the fiber optic bundle. It will be appreciated that light loses coherence momentarily as the geometry of its path changes. When the new path comes to rest, a new speckle pattern will appear. Introducing vibration to the fiber is essentially introducing a series of changes in path geometry, and if the change in path geometry is performed at a fast enough frequency the observable speckle pattern may be substantially eliminated or removed, such that a human eye cannot detect the speckle pattern.

When viewed by the human eye, the minimum oscillation frequency to remove observable speckle is approximately 20 Hz. If the image is being captured by an imaging sensor, this minimum frequency could change based on the image acquisition frame rate and the display frame rate.

Figure 1A:
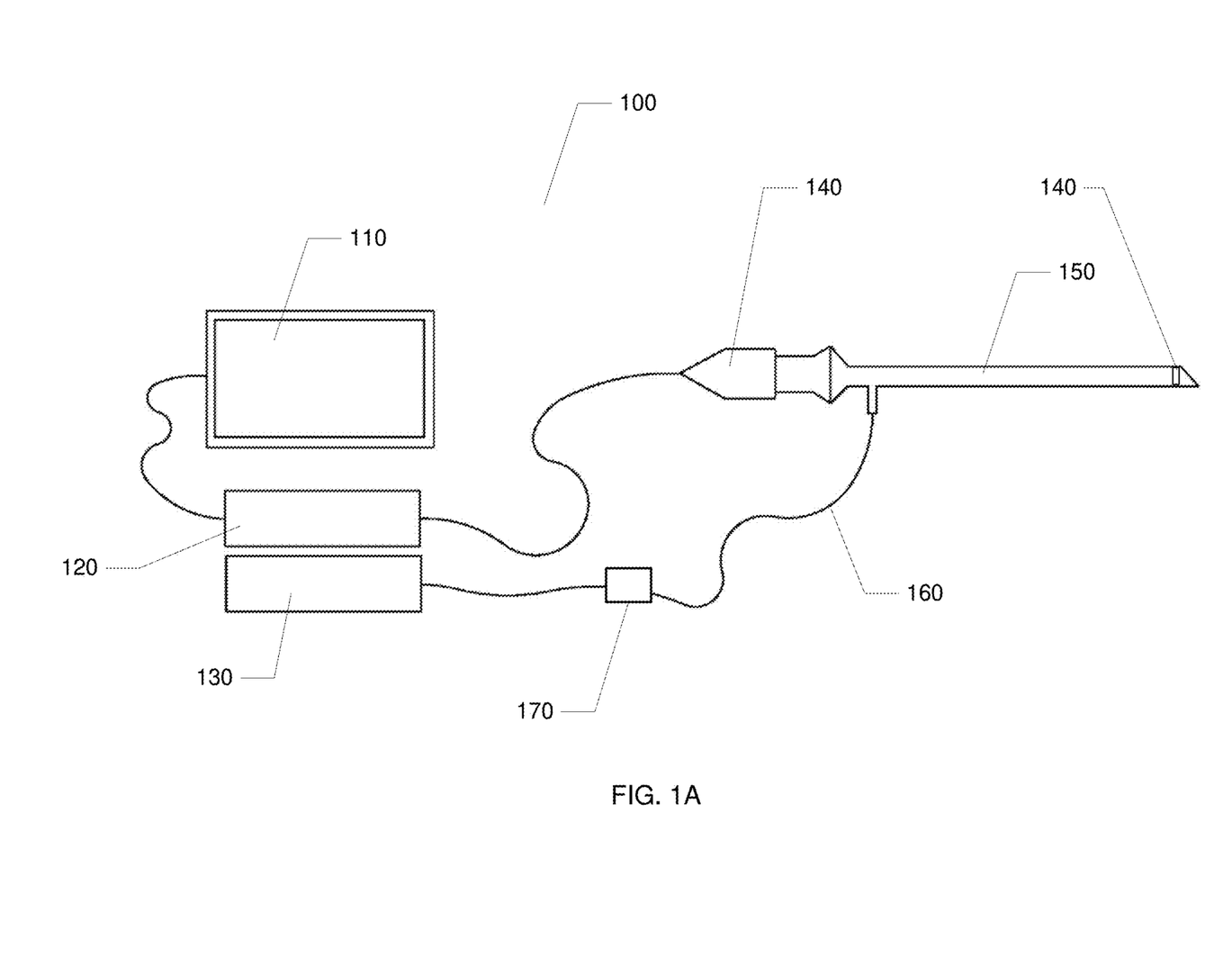
FIGS. 1A and 1B illustrate implementations of a system for removing speckle from a coherent light source, such as laser light in accordance with the teachings and principles of the disclosure.
Figure 1B:
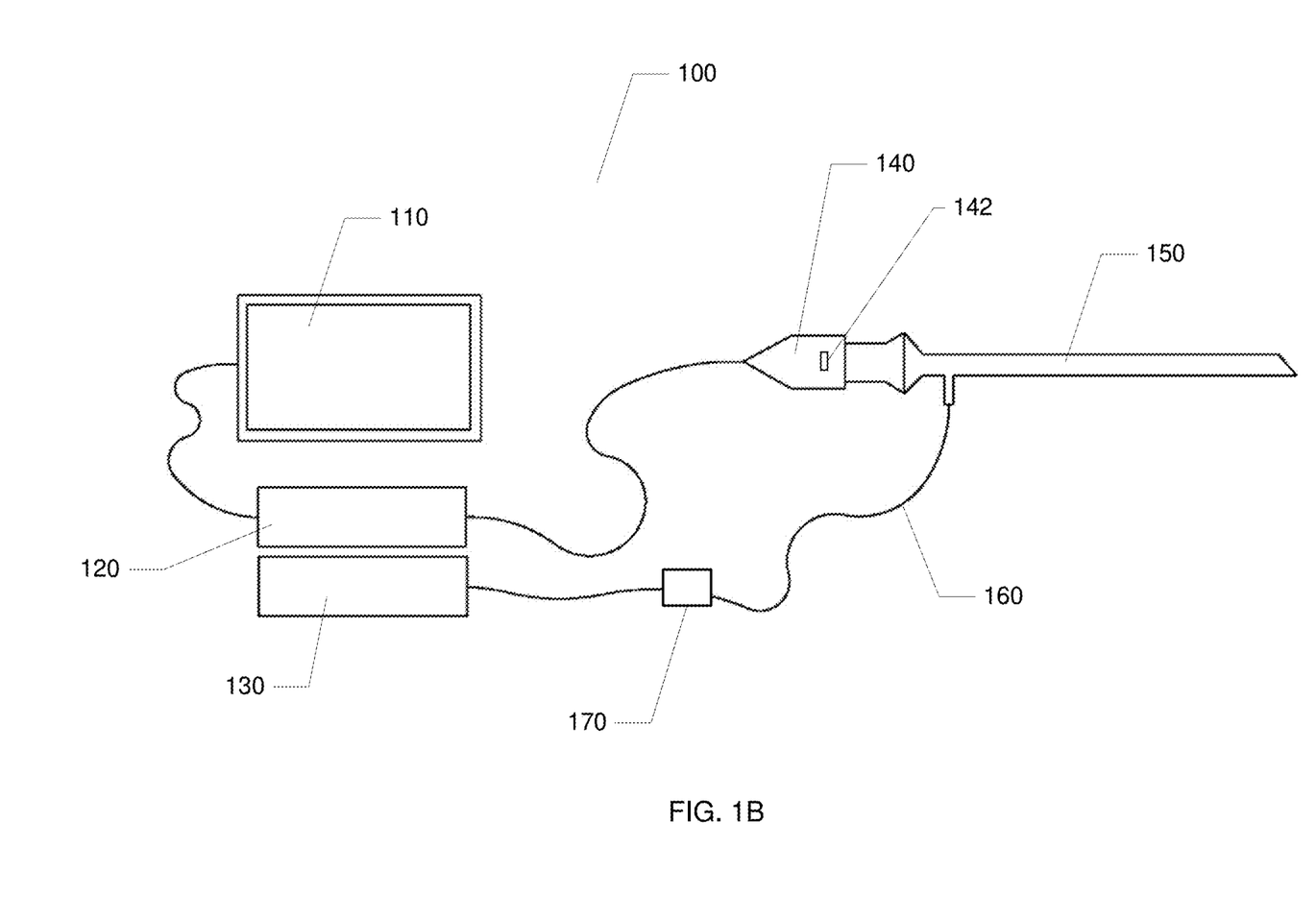

Referring now to FIGS. 1A and 1B, a system 100 for removing speckle from a coherent light source, such as laser light, is illustrated. The system 100 may comprise a display 110, a control unit 120, a coherent light source 130, such as a laser light source, an imaging device 140, such as a camera that may be in electronic communication with the control unit 120 and/or the light source 130, an endoscopic device 150, a fiber optic bundle 160, and a vibrating mechanism 170.

In the implementation of FIG. 1A, an image sensor 142 may be located at a distal end of the endoscopic device 150 as detailed more fully below. In the implementation of FIG. 1B, the imaging sensor 142 may be located in the imaging device 140.

Figure 2:
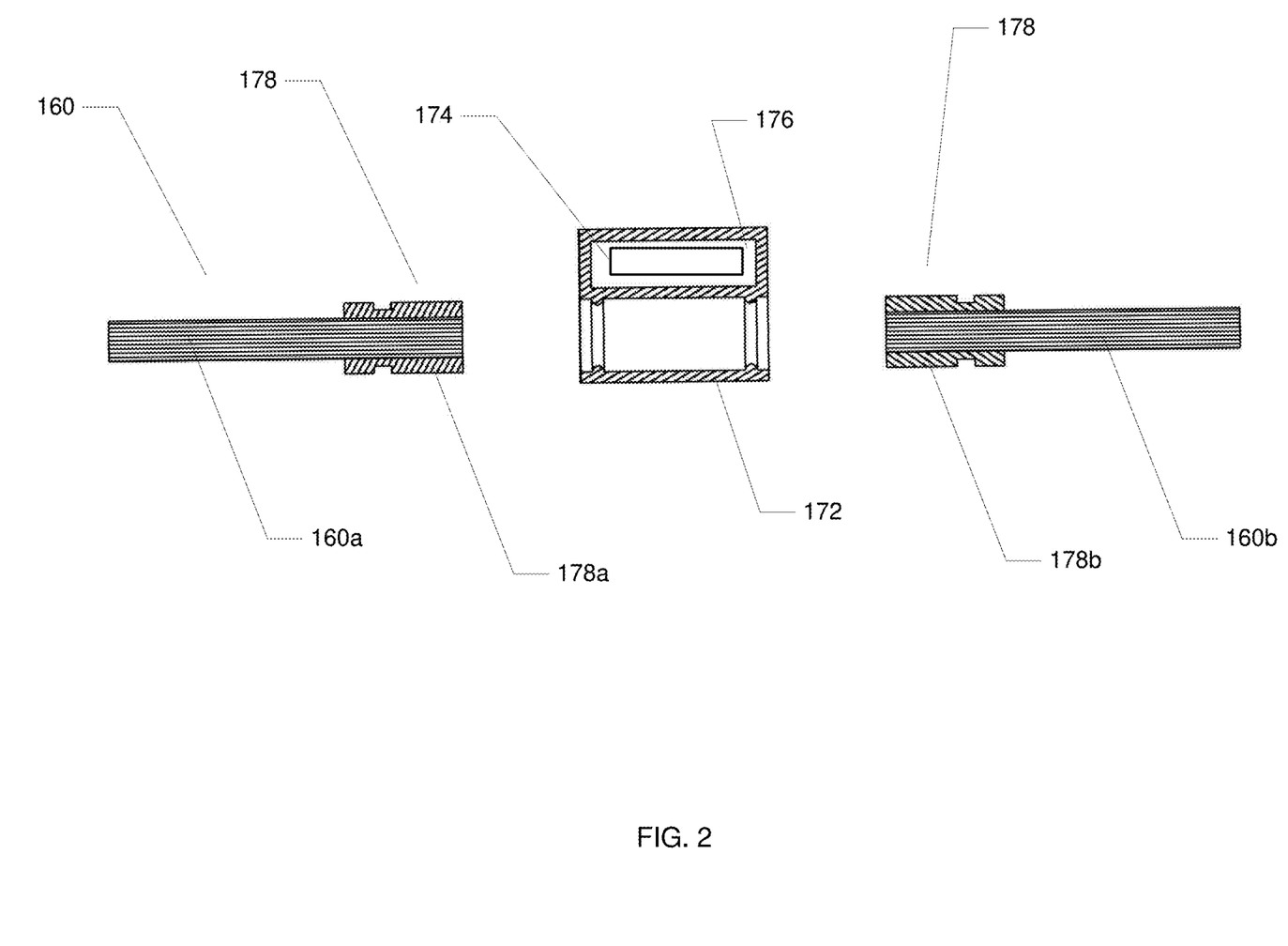
FIG. 2 illustrates a side, exploded view of a device for removing speckle from a scene lit by a coherent light source, such as laser light, according to one implementation and in accordance with the teachings and principles of the disclosure.
Figure 3:
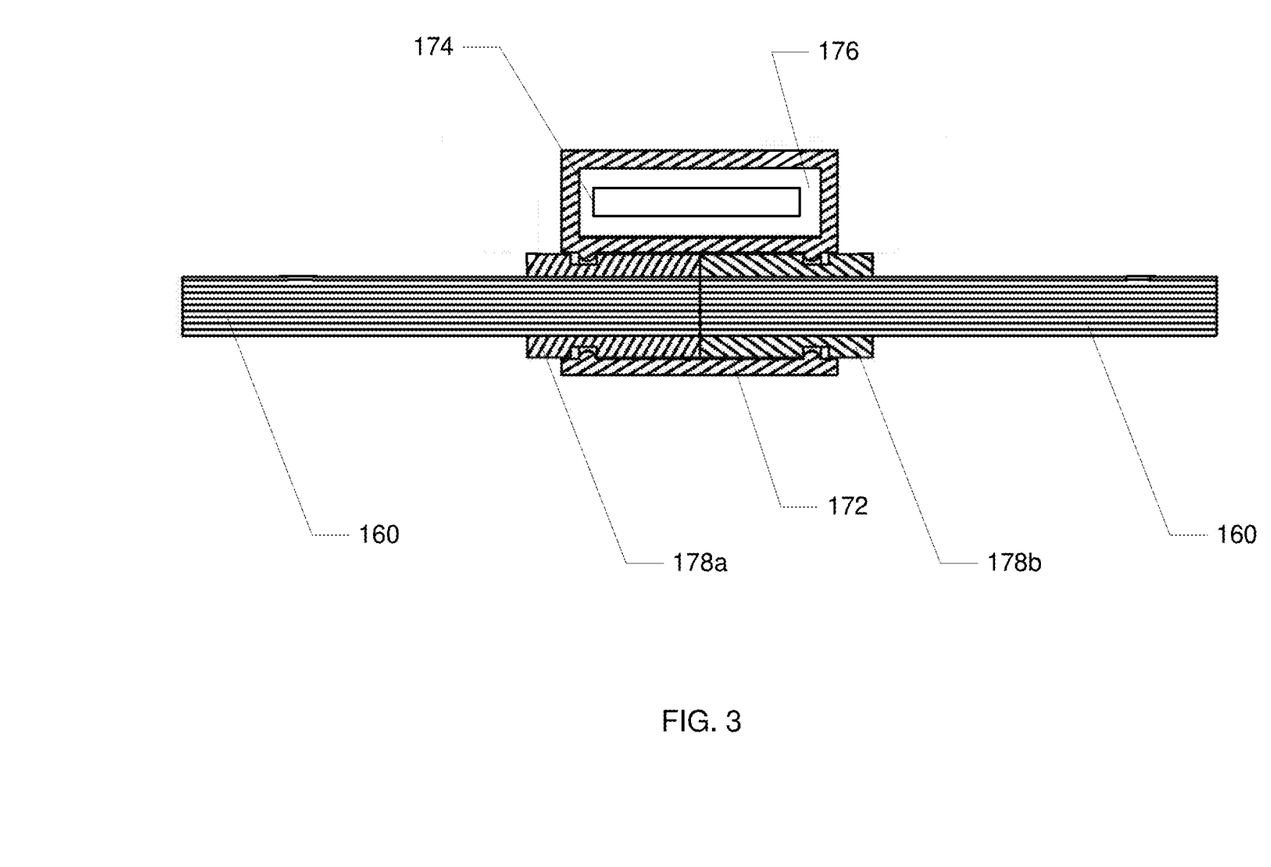
FIG. 3 illustrates a side view of a device for removing speckle from scene lit by a coherent light source, such as laser light, according to one implementation and in accordance with the teachings and principles of the disclosure.

Referring now to FIGS. 2 and 3, the vibrating mechanism 170 for removing speckle from the coherent light source 130 is illustrated. The vibrating mechanism 170 may comprise a connector 172, a vibrating device 174, a cavity 176 formed within the connector 172 for receiving and holding the vibrating device 174 therein, and a sleeve 178. It will be appreciated that the sleeve 178 may comprise a single sleeve 178, or a plurality of sleeves 178, such as a first sleeve 178a and a second sleeve 178b. The first sleeve 178a and the second sleeve 178b may be used for attaching a first fiber optic bundle 160a and a second fiber optic bundle 160b, respectively, as illustrated in FIGS. 2 and 3. It will be appreciated that the vibrating mechanism may simply comprise the vibrating device 174 without departing from the scope of the disclosure. The vibrating device 174 may be a small mechanical motor, or a piezoelectric crystal, oscillator, or resonator component. It will be appreciated that the vibrating device 174 may be selected from the group consisting of a small mechanical motor, or a piezoelectric crystal, oscillator, or resonator component.

The vibrating mechanism 170 may be located or placed anywhere along the fiber optic bundle 160. The vibrating mechanism 170 causes the light emanating from the light source, such as laser light, to lose coherence momentarily as the geometry of its path is changed. When the new path comes to rest, a new speckle pattern will appear. The introduction of the vibration or vibration stimulus to the fiber optic bundle 160 introduces a series of changes in path geometry. The series of changes should be performed at a high enough frequency so that the observable speckle pattern may be substantially eliminated or removed, such that a human eye cannot detect the speckle pattern when the video is output to the display 110.

In one implementation, the vibrating mechanism 170 may be located or placed at a junction or connection point of two lengths of fiber 160, as illustrated in FIGS. 2 and 3. In this implementation, the vibrating mechanism 170 may be integrated into the connector 172 that acts to couple the two lengths of the fiber 160 as illustrated best in FIG. 3.

In one implementation, the vibrating mechanism 170 may be coupled to a single location, instead of a plurality of locations, along a length of the fiber bundle 160.

In any implementation, a vibration damper may be utilized to minimize the vibration experienced by the user. The vibration damper may be located anywhere along the fiber optic bundle to reduce the amplitude of oscillations or vibrations so that the user of the imaging device does not experience or receive the oscillations or vibrations.

Figure 4:
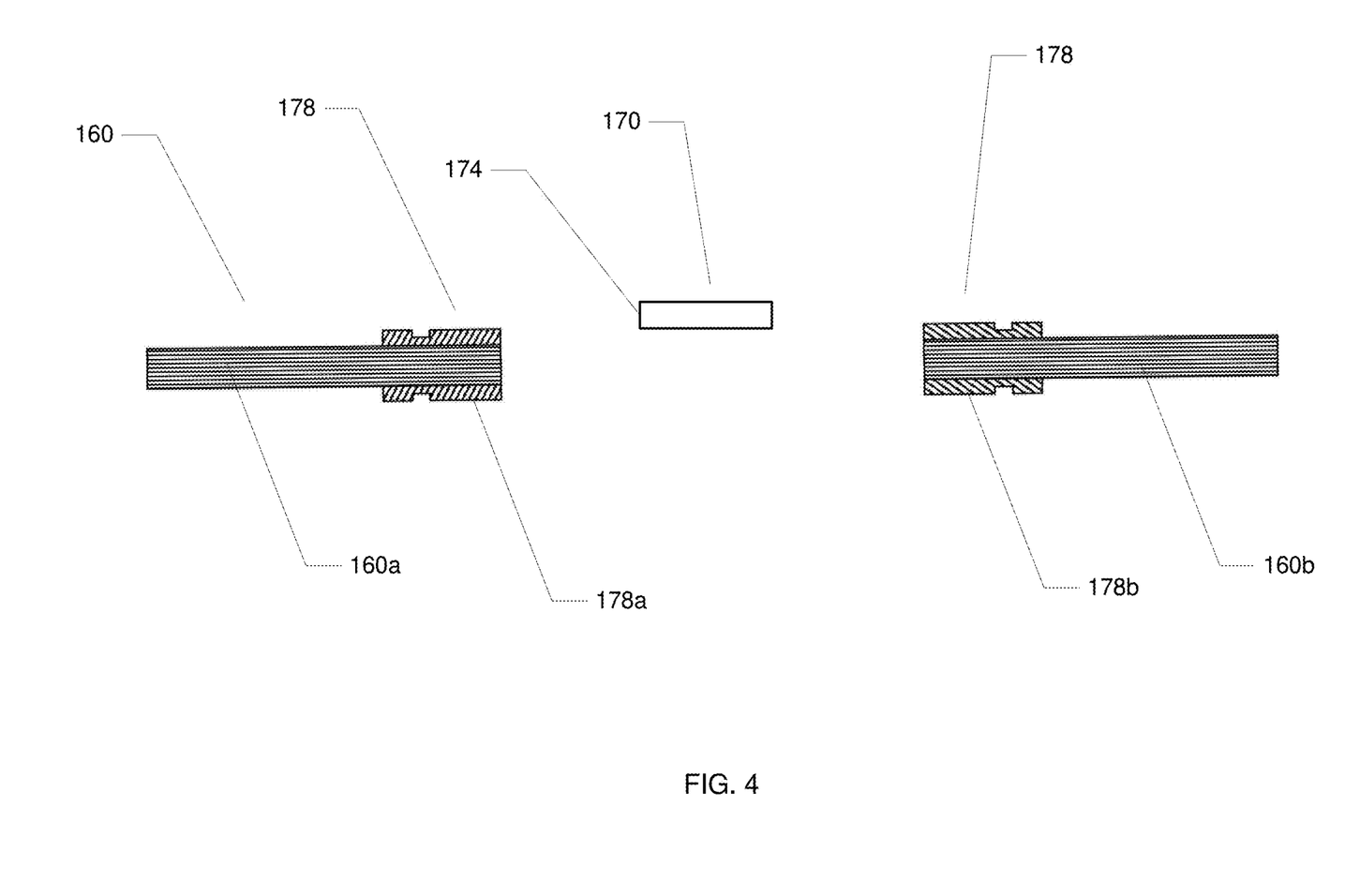
FIG. 4 illustrates a side, exploded view of a device for removing speckle from a scene lit by a coherent light source, such as laser light, according to one implementation and in accordance with the teachings and principles of the disclosure.
Figure 5:
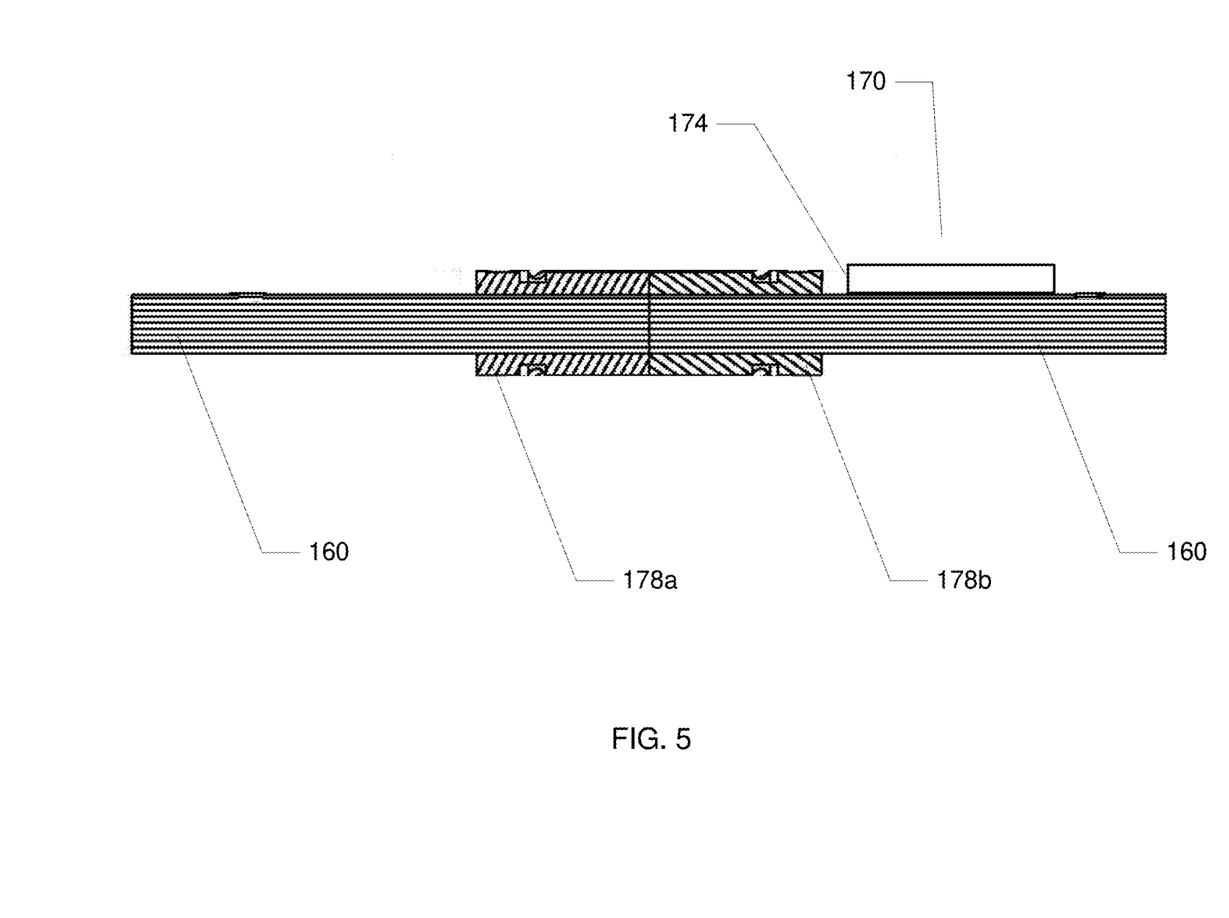
FIG. 5 illustrates a side view of a device for removing speckle from scene lit by a coherent light source, such as laser light, according to one implementation.

In an implementation, the vibrating mechanism 170 may comprise a vibrating device 174 that may only be attached to the fiber optic bundle 160. In this implementation, the vibrating device 174 is directly attached to the fiber optic bundle 160 with no intervening connectors or parts as illustrated best in FIGS. 4 and 5. In this implementation, the vibrating device 174 may be a small mechanical motor, a piezoelectric crystal, an oscillator, and a resonator component. It will be appreciated that the vibrating device 174 of this implementation may be selected from the group consisting of a small mechanical motor, or a piezoelectric crystal, oscillator, or resonator component.

The imaging device 140 of the system 100 for removing speckle from an image frame from a surgical site may comprise the image sensor 142, wherein the image sensor comprises a pixel array 144. Similarly, the image sensor 142 may be located at a distal portion of the endoscopic device 150. It will be appreciated that the endoscopic device 150 of the disclosure may be any suitable endoscopic device that is known or that may become known in the future that may be used in a surgical setting without departing from the scope of the disclosure.

The coherent light source 130 for providing light to a surgical site may be any suitable coherent light source that is known or that may become known in the future that may be used in a surgical setting without departing from the scope of the disclosure. It will be appreciated that the fiber optic bundle 160 may be connected to the coherent light source 130 and to the endoscopic device 150 as illustrated in FIGS. 1A and 1B. It will be appreciated that any suitable fiber optic bundle that is known or that may become known in the future that may be used in a surgical setting may be utilized by the disclosure without departing from the scope of the disclosure.

The control unit 120 may comprise circuitry for sending data to the image sensor 142 and receiving data from the image sensor 142 to create an image frame of the surgical site. The control unit 120 may be any suitable control unit that is known or that may become known in the future that may be used in a surgical setting without departing from the scope of the disclosure. Similarly, the display of the disclosure allows a user to visualize the surgical site and may be any suitable display that is known or that may become known in the future that may be used in a surgical setting without departing from the scope of the disclosure.

It will be appreciated that the imaging device 140 of the system 100 may be in electronic communication with the control unit 120. In an implementation, the imaging sensor 142 may be a CMOS sensor. In an implementation, the imaging sensor may be a CCD sensor.

It will be appreciated that the above disclosure may be applied to any MIS or endoscopy visualization system using a laser-based light source, including a conventional reusable system, a limited use or re-posable system, or a single use system. This is also applicable for white or colored laser light sources within the visible spectrum or outside the visible spectrum.

Figure 6:
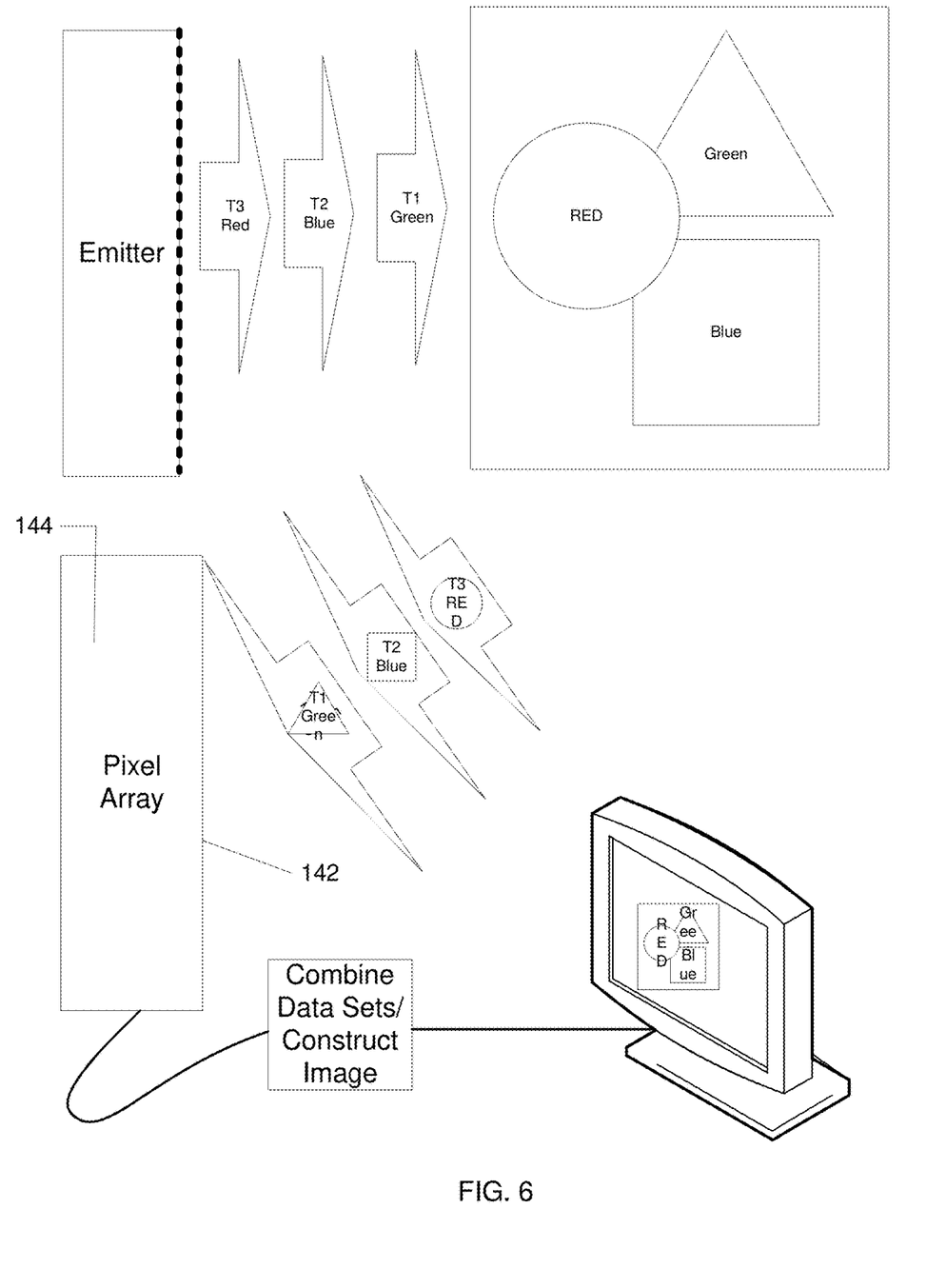
FIG. 6 illustrates a schematic view of a paired sensor and an electromagnetic emitter in operation for use in producing an image in a light deficient environment in accordance with the teachings and principles of the disclosure.

Referring now to FIGS. 6-9B, it will be appreciated that the principles and teachings of the disclosure may be applied to many different endoscopic and imaging systems. For example, the vibrating mechanism 170 used to remove speckle may be used in combination with a monochrome image sensor and a pulsing laser light source. FIG. 6 illustrates a schematic view of a paired sensor and an electromagnetic emitter in operation for use in producing an image in a light deficient environment. Such a configuration allows for increased functionality in light controlled or ambient light deficient environments. It should be noted that as used herein the term "light" is both a particle and a wavelength, and is intended to denote electromagnetic radiation that is detectable by a pixel array, and may be include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. An emitter may be a light source that is controllable as to the portion of the electromagnetic spectrum that is emitted, the intensity of the emissions, or the duration of the emission, or all three. An emitter may emit light in any dithered, diffused, or columnated emission and may be controlled digitally or through analog methods or systems.

A pixel array of an image sensor may be paired with an emitter electronically, such that they are synced during operation for both receiving the emissions and for the adjustments made within the system. As can be seen in FIG. 6, an emitter may be tuned to emit electromagnetic radiation in the form of a laser, which may be pulsed in order to illuminate an object. The emitter may pulse at an interval that corresponds to the operation and functionality of a pixel array. The emitter may pulse light in a plurality of electromagnetic partitions, such that the pixel array receives electromagnetic energy and produces a data set that corresponds (in time) with each specific electromagnetic partition. For example, FIG. 6 illustrates a system having a monochromatic pixel array (black and white), which is simply sensitive to electromagnetic radiation of any wavelength. The light emitter illustrated in the figure may be a laser emitter that is capable of emitting a green electromagnetic partition, a blue electromagnetic partition, and a red electromagnetic partition in any desired sequence. It will be appreciated that other light emitters may be used in FIG. 6 without departing from the scope of the disclosure, such as digital based emitters that create a speckle pattern. During operation, the data created by the monochromatic sensor for any individual pulse is assigned a specific color partition, wherein the assignment is based on the timing of the pulsed color partition from the emitter. Even though the pixels are not color dedicated they can be assigned a color for any given data set based on timing. In one implementation, three data sets representing RED, GREEN and BLUE pulses may then be combined to form a single image frame. It will be appreciated that the disclosure is not limited to any particular color combination or any particular electromagnetic partition, and that any color combination or any electromagnetic partition may be used in place of RED, GREEN and BLUE, such as Cyan, Magenta and Yellow, Ultraviolet, infra-red, or any other color combination, including all visible and non-visible wavelengths, without departing from the scope of the disclosure. In the figure, the object to be imaged contains a red portion, green portion and a blue portion. As illustrated in the figure, the reflected light from the electromagnetic pulses only contains the data for the portion of the object having the specific color that corresponds to the pulsed color partition. Those separate color (or color interval) data sets can then be used to reconstruct the image by combining the data sets.

The disclosure is also concerned with a system solution for endoscopy applications in which the image sensor is resident at the distal end of the endoscope. In striving for a minimal area sensor based system, there are other design aspects that can be developed too, beyond the reduction in pixel count. In particular, the area of the digital portion of the chip should be minimized, as should the number of connections to the chip (pads). This involves the design of a full-custom CMOS image sensor with several novel features.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Figure 7A:
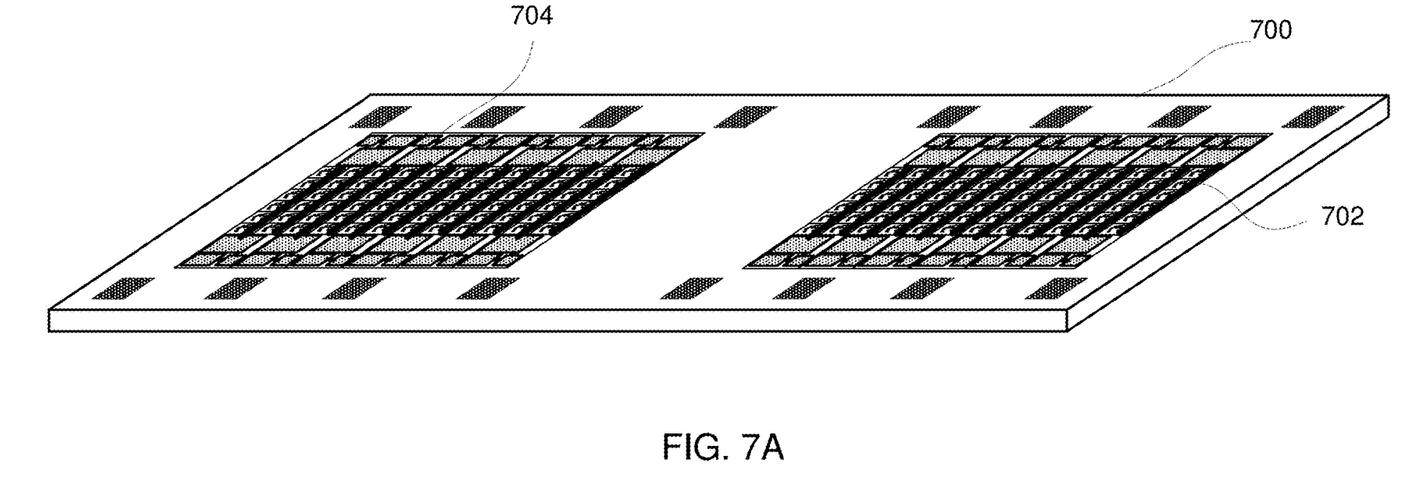
FIGS. 7A and 7B illustrate a perspective view and a side view, respectively, of an implementation of a monolithic sensor having a plurality of pixel arrays for producing a three dimensional image in accordance with the teachings and principles of the disclosure.
Figure 7B:
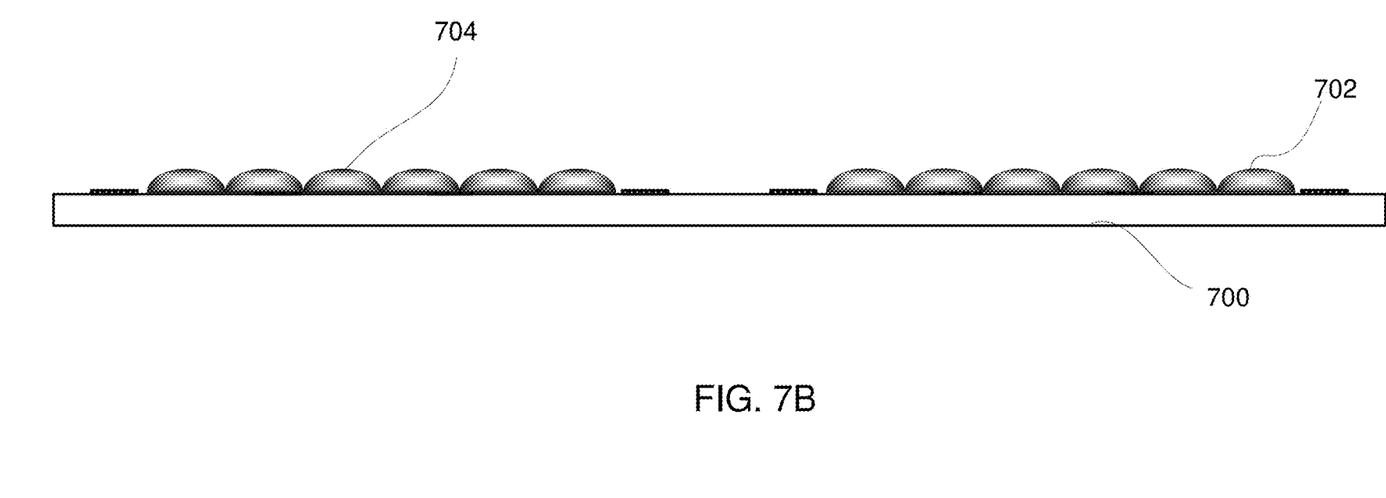

Referring now to FIGS. 7A and 7B, the figures illustrate a perspective view and a side view, respectively, of an implementation of a monolithic sensor 700 having a plurality of pixel arrays for producing a three dimensional image in accordance with the teachings and principles of the disclosure. Such an implementation may be desirable for three dimensional image capture, wherein the two pixel arrays 702 and 704 may be offset during use. In another implementation, a first pixel array 702 and a second pixel array 704 may be dedicated to receiving a predetermined range of wave lengths of electromagnetic radiation, wherein the first pixel array 702 is dedicated to a different range of wave length electromagnetic radiation than the second pixel array 704.

Figure 8A:
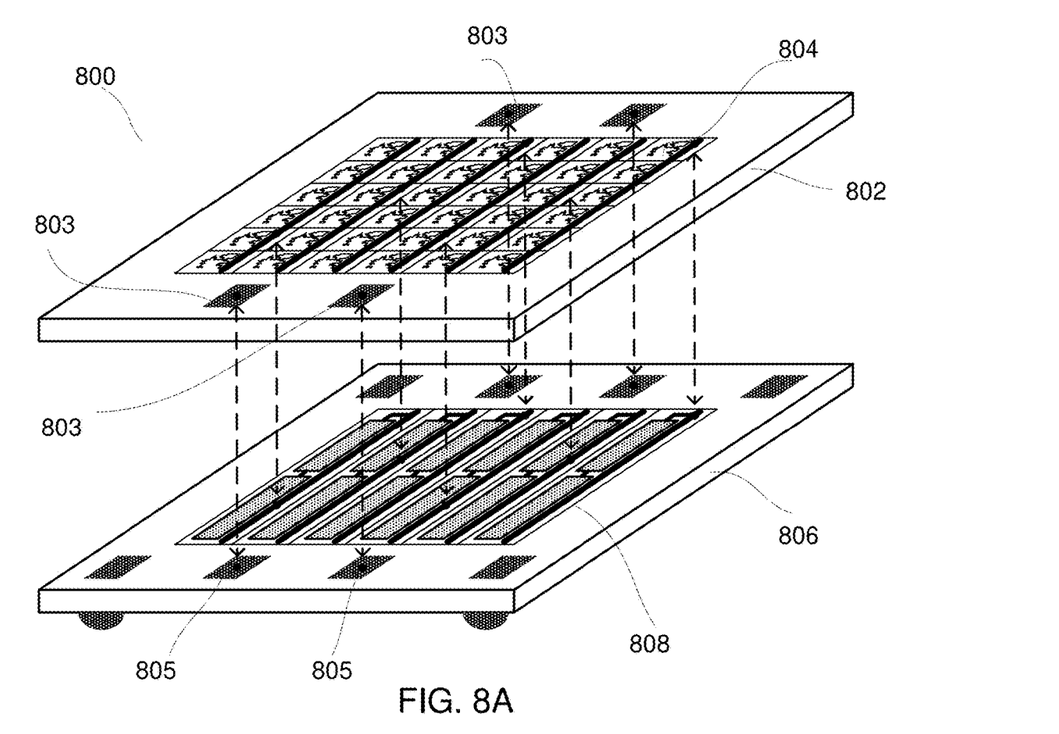
FIGS. 8A and 8B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 8B:
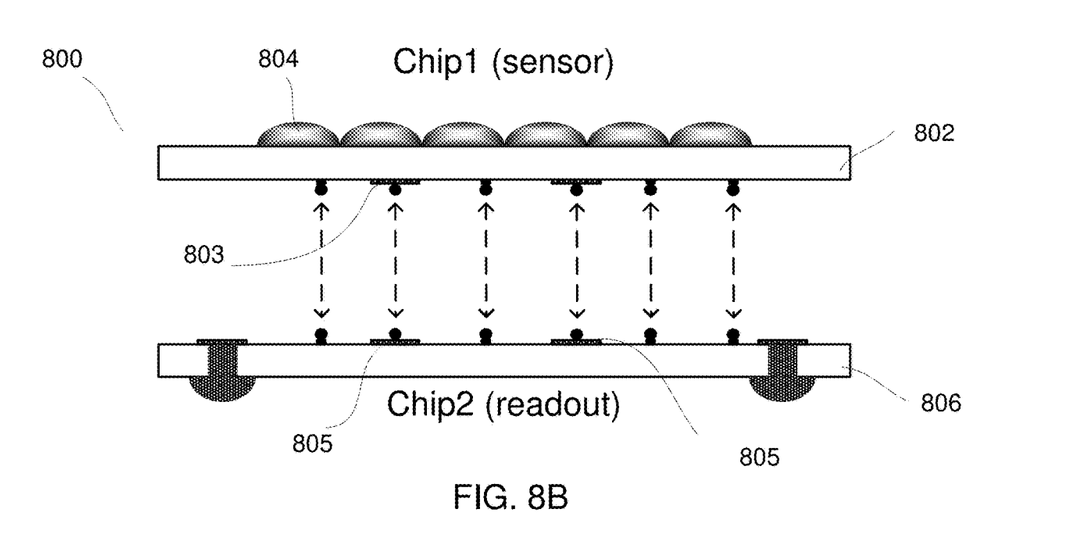

FIGS. 8A and 8B illustrate a perspective view and a side view, respectively, of an implementation of an imaging sensor 800 built on a plurality of substrates. As illustrated, a plurality of pixel columns 804 forming the pixel array are located on the first substrate 802 and a plurality of circuit columns 808 are located on a second substrate 806. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 802 of the two substrates/chips may be processed using an image CMOS process. The first substrate/chip 802 may be comprised either of a pixel array exclusively or a pixel array surrounded by limited circuitry. The second or subsequent substrate/chip 806 may be processed using any process, and does not have to be from an image CMOS process. The second substrate/chip 806 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 802 may be stacked with the second or subsequent substrate/chip 806 using any three-dimensional technique. The second substrate/chip 806 may support most, or a majority, of the circuitry that would have otherwise been implemented in the first image CMOS chip 802 (if implemented on a monolithic substrate/chip) as peripheral circuits and therefore have increased the overall system area while keeping the pixel array size constant and optimized to the fullest extent possible. The electrical connection between the two substrates/chips may be done through interconnects 803 and 805, which may be wirebonds, bump and/or TSV (Through Silicon Via).

Figure 9A:
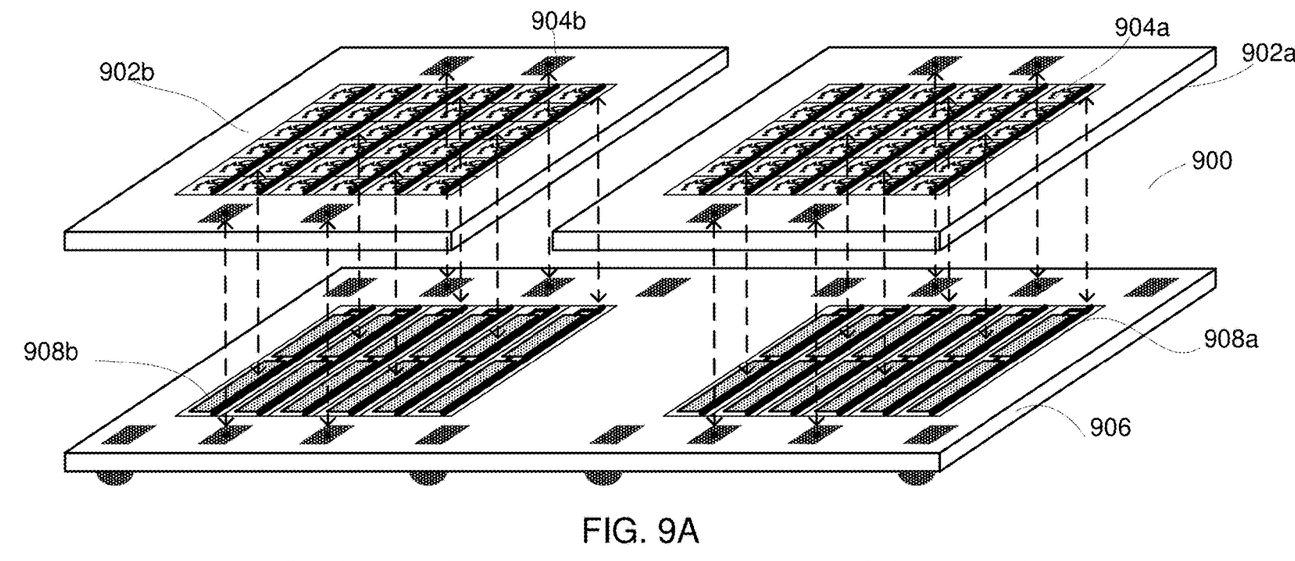
FIGS. 9A and 9B illustrate a perspective view and a side view, respectively, of an implementation of an imaging sensor having a plurality of pixel arrays for producing a three dimensional image, wherein the plurality of pixel arrays and the image sensor are built on a plurality of substrates.
Figure 9B:
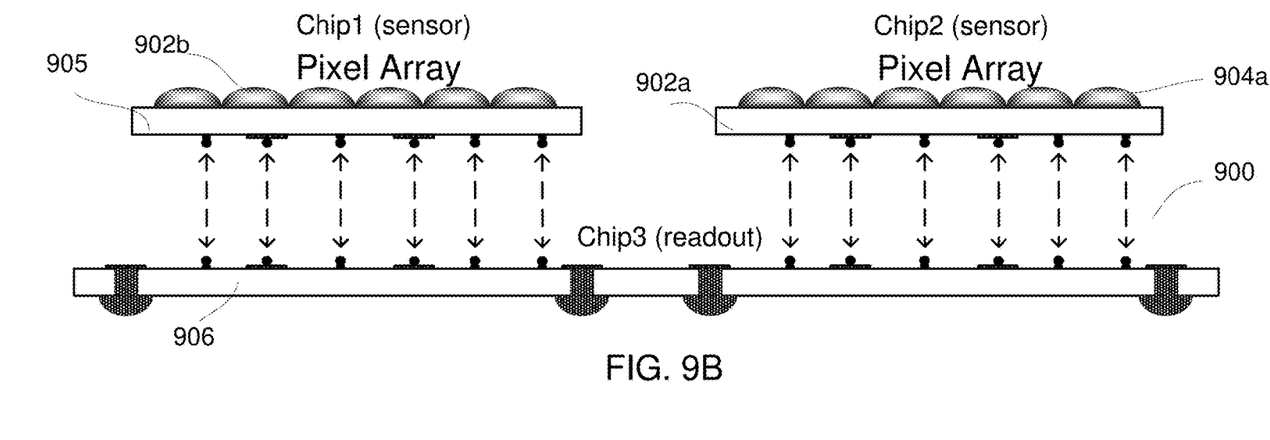

FIGS. 9A and 9B illustrate a perspective view and a side view, respectively, of an implementation of an imaging sensor 900 having a plurality of pixel arrays for producing a three dimensional image. The three dimensional image sensor may be built on a plurality of substrates and may comprise the plurality of pixel arrays and other associated circuitry, wherein a plurality of pixel columns 904a forming the first pixel array and a plurality of pixel columns 904b forming a second pixel array are located on respective substrates 902a and 902b, respectively, and a plurality of circuit columns 908a and 908b are located on a separate substrate 906. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method for removing speckle from an image frame depicting a surgical site, the method comprising:
    instructing an emitter to emit coherent light, wherein the coherent light is transmitted to a surgical site by way of a fiber optic bundle, and wherein the fiber optic bundle comprises:
        a first fiber optic bundle;
        a second fiber optic bundle; and
        a vibrating connector that couples the first fiber optic bundle to the second fiber optic bundle;
    actuating the vibrating connector to vibrate the first fiber optic bundle and the second fiber optic bundle to cause the coherent light to lose coherence;
    causing an image sensor of an endoscopic device to output a dataset, wherein the dataset corresponds in time with emission of the coherent light by the emitter; and
    creating the image frame depicting the surgical site based on the dataset.

2. The method of claim 1, wherein actuating the vibrating connector comprising instructing the vibrating connector to introduce a vibration stimulus to the first fiber optic bundle and the second fiber optic bundle to thereby create a series of changes in path geometry along the fiber optic bundle.

3. The method of claim 2, wherein the series of changes in the path geometry are performed at a high frequency such that an observable speckle pattern in the plurality of datasets is substantially removed.

4. The method of claim 1, further comprising electronically conveying the dataset from the image sensor to a control unit of the endoscopic device, and wherein creating the image frame depicting the surgical site comprises creating with the control unit.

5. The method of claim 1, wherein the fiber optic bundle further comprises a sleeve disposed around the vibrating connector.

6. The method of claim 1, wherein the vibrating connector comprises one or more of a mechanical motor, a piezoelectric crystal, an oscillator, or a resonator.

7. The method of claim 5, wherein the sleeve comprises:
   a first sleeve configured to attach the vibrating connector to the first fiber optic bundle; and
   a second sleeve configured to attach the vibrating connector to the second fiber optic bundle.

8. The method of claim 1, further comprising substantially removing speckle from the image frame depicting the surgical site.

9. The method of claim 1, further comprising displaying the image frame depicting the surgical site on a display to enable a user to visualize the surgical site.

10. The method of claim 1, wherein the fiber optic bundle further comprises a vibrating dampener to control an amount of vibration performed by the vibrating connector.

11. The method of claim 1, wherein the vibrating connector is integrated into the first fiber optic bundle or the second fiber optic bundle.

12. The method of claim 1, wherein the image sensor is a complementary metal oxide semiconductor (CMOS) sensor.

13. The method of claim 1, wherein the image sensor is a charge-coupled device (CCD) sensor.

14. The method of claim 1, wherein the vibrating connector comprises a vibrating device that is only attached to the fiber optic bundle.

15. The method of claim 14, wherein the vibrating device comprises one or more of a mechanical motor, a piezoelectric crystal, an oscillator, or a resonator component.

16. The method of claim 1, wherein the vibrating connector comprises a vibrating device disposed in a cavity formed in the vibrating connector.

17. The method of claim 16, wherein the vibrating connector is the only vibrating mechanism along a path of the fiber optic bundle that vibrates both the first fiber optic bundle and the second fiber optic bundle, and further causes the coherent light to lose coherence momentarily as a geometry of the path of the fiber optic bundle is changed by vibration.

18. The method of claim 1, wherein instructing the emitter to emit the coherent light comprises instructing the emitter to emit a plurality of pulses of coherent light in a plurality of partitions of electromagnetic radiation;
   wherein the image sensor outputs a plurality of datasets; and
   wherein each of the plurality of datasets corresponds in time with at least one pulse of the plurality of pulses of coherent light.

19. The method of claim 18, further comprising assigning each of the plurality of datasets a partition of electromagnetic radiation based on timing of the plurality of pulses of coherent light emitted by the emitter.

20. The method of claim 19, wherein the plurality of pulses of coherent light comprises:
   a plurality of pulses of electromagnetic radiation within a visible waveband of the electromagnetic spectrum; and
   a plurality of pulses of electromagnetic radiation within an infrared waveband of the electromagnetic spectrum.

* * * * *